(12) United States Patent
Terrill et al.

(10) Patent No.: US 12,029,440 B2
(45) Date of Patent: Jul. 9, 2024

(54) REAMER FOR AUGMENTED GLENOID IMPLANT

(71) Applicant: Howmedica Osteonics Corp., Mahwah, NJ (US)

(72) Inventors: Lance N. Terrill, League City, TX (US); Michael Shabelman, Fair Lawn, NJ (US); Sunny Shorabh, Ghaziabad (IN)

(73) Assignee: Howmedica Osteonics Corp., Mahwah, NJ (US)

( * ) Notice: Subject to any disclaimer, the term of this patent is extended or adjusted under 35 U.S.C. 154(b) by 540 days.

(21) Appl. No.: 17/308,493

(22) Filed: May 5, 2021

(65) Prior Publication Data

US 2021/0378685 A1   Dec. 9, 2021

Related U.S. Application Data

(60) Provisional application No. 63/034,585, filed on Jun. 4, 2020.

(51) Int. Cl.
*A61B 17/16* (2006.01)

(52) U.S. Cl.
CPC ...... *A61B 17/1659* (2013.01); *A61B 17/1684* (2013.01)

(58) Field of Classification Search
CPC ............ A61B 17/1684; A61B 17/1659; A61B 17/1778
See application file for complete search history.

(56) References Cited

U.S. PATENT DOCUMENTS

| 10,028,838 | B2 | 7/2018 | Hodorek et al. | |
|---|---|---|---|---|
| 2008/0119860 | A1* | 5/2008 | McCarthy | A61B 17/15 606/82 |
| 2012/0197258 | A1* | 8/2012 | Chavarria | A61B 17/1735 606/85 |
| 2014/0039505 | A1 | 2/2014 | Anthony et al. | |
| 2018/0193037 | A1 | 7/2018 | Anthony et al. | |

OTHER PUBLICATIONS

DePuy Synthes Joint Reconstruction, Global Steptech Anchor Peg Glenoid Surgical Technique, 2014, pp. 1-32, DePuy Orthopaedics, Inc.
Knowles, et al., Augmented glenoid component designs for type B2 erosions: a computational comparison by volume of bone removal and quality of remaining bone, Journal of Shoulder and Elbow Surgery, 2015, pp. 1218-1226, vol. 24.
Knowles, et al., The arthritic glenoid anatomy and arthroplasty designs, Curr Rev Musculoskelet Med, published online Jan. 2016, pp. 23-29, vol. 9.
Knowles, Osteoarthritis Induced Glenoid Morphology and Bone Quality: An Evaluation of Augmented Glenoid Components, Electronic Thesis and Dissertation Repository, Apr. 2015, pp. 1-172, 2752.

* cited by examiner

*Primary Examiner* — Andrew Yang
(74) *Attorney, Agent, or Firm* — Lerner David LLP

(57) ABSTRACT

A reaming device for preparing a glenoid of a patient may include a base configured for mounting to bone and an oscillatory rasp configured to be translatable in a proximal-distal direction relative to the base while the base is coupled to the glenoid of the patient.

19 Claims, 12 Drawing Sheets

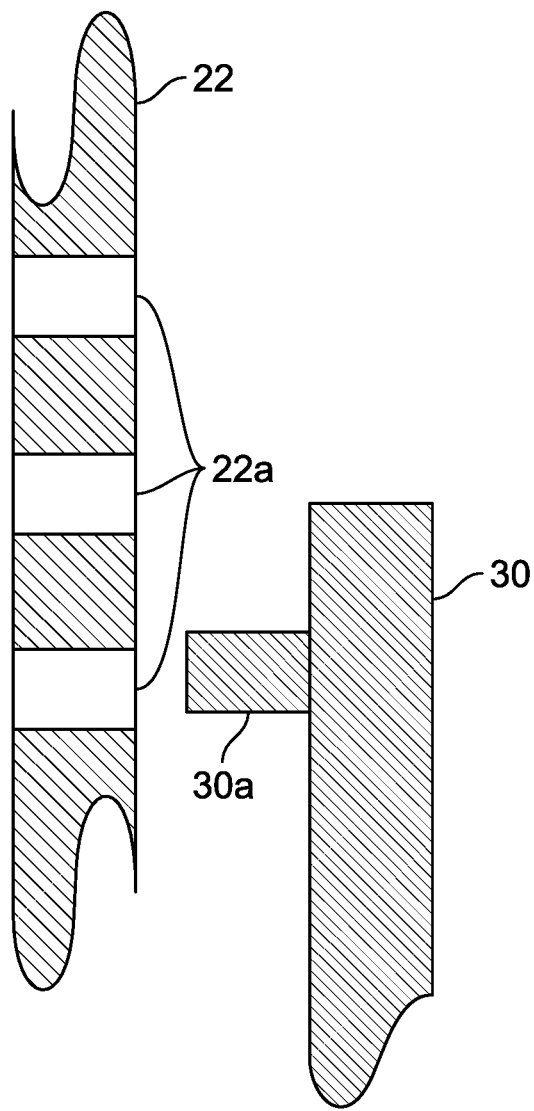# 
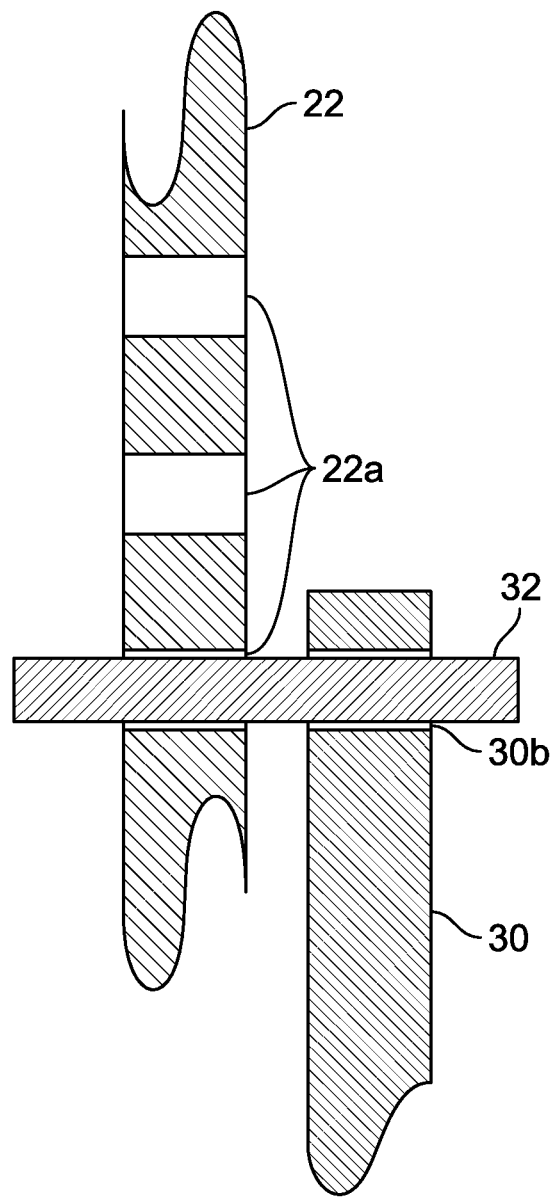
FIG. 4A    FIG. 4B

REAMER FOR AUGMENTED GLENOID IMPLANT

CROSS-REFERENCE TO RELATED APPLICATIONS

This application claims the benefit of the filing date of U.S. Provisional Patent Application No. 63/034,585, filed Jun. 4, 2020, the disclosure of which is hereby incorporated herein by reference.

BACKGROUND

Eccentric glenoid erosion occurs in as much as 40% of shoulder arthroplasty candidates. Wear can present anteriorly, superiorly, and posteriorly, with superior being most common in reverse shoulder arthroplasty ("RSA") candidates, and posterior being most prevalent in total shoulder arthroplasty ("TSA") candidates. As the articular surface of the glenoid wears or degrades over time, the glenoid surface may take a biconcave shape. The worn or degraded portion of the glenoid may be referred to as the neoglenoid and the original portion of the glenoid may be referred to as the paleoglenoid.

Any glenoid implant that does not have a biconvex design to match the concave surface of a glenoid with eccentric glenoid erosion may require removal of a relatively large amount of bone stock, including portions of the paleoglenoid, which may be undesirable. As eccentric glenoid erosion progresses, the relative sizes and shapes of the paleoglenoid and the neoglenoid may also change. Therefore, to minimize removal of bone stock, a range of biconvex designs corresponding to various stages of erosion may be used. One exemplary biconvex design is illustrated in FIGS. 1A and 1B. The implant 1 of FIGS. 1A and 1B includes a biconvex bone-facing surface 3 and an opposing concave surface 5. The concave surface 5 serves as a replacement for the natural glenoid cavity after the implant 1 is placed on the bone. The bone-facing surface 3 includes a first convex portion 3a configured to mate to the prepared paleoglenoid, and a second convex portion 3b configured to mate to the prepared neoglenoid. The second convex portion 3b is angled relative to the first convex portion 3b to match the anticipated angle between the prepared paleoglenoid and neoglenoid surfaces. As shown in FIG. 1C, the implant 1 may be provided in multiple variations corresponding to different degrees along a typical eccentric erosion pattern for a natural glenoid cavity. The second convex portion 3b is larger compared to the first convex portion 3a in implants 1 corresponding to progressively greater degrees of erosion. Three implants 1 corresponding to three different degrees of erosion are shown in FIG. 1C, but more or fewer implants may be provided in various examples. Preparation of a glenoid for such biconvex implants may be facilitated by a tool able to accommodate both the stage of erosion and the selected implant.

BRIEF SUMMARY OF THE DISCLOSURE

The present disclosure relates to a device that may be used for preparing a glenoid cavity exhibiting eccentric erosion for a biconvex glenoid implant. The device may include a base and a rasp being adjustable relative to one another. Specifically, the base and the rasp may be adjustable relative to one another along a proximal-distal axis such that a distance that the rasp extends distally beyond the base may be varied. The rasp may be configured to oscillate about a pivot axis, and the adjustment of the base and rasp relative to one another may include movement or translation of the features defining the pivot axis relative to the base, or movement or translation of the base relative to the features defining the pivot axis. The base and rasp may be adjusted relative to one another before fixing the base to the paleoglenoid. The base and rasp may be adjusted again after the rasp has removed some of the neoglenoid, such as by moving the rasp distally further beyond the base to reengage the new surface of the neoglenoid.

The device may include an assembly for converting rotational input into oscillating output. The assembly may include a shaft arranged to be driven rotationally about the shaft's centerline. The shaft may include a hammer offset from the shaft's centerline. An anvil may include a pair of prongs extending along opposite sides of the hammer, and the anvil may be arranged and constrained such that rotation of the shaft causes the hammer to strike the prongs in alternation, which may in turn cause the anvil to pivot back and forth in an oscillating pattern relative to the pivot axis. The pivot axis may be defined by a pivot pin suspending the anvil relative to the device. Alternatively, the pivot axis may be defined by a guidewire or post disposed through the rasp and extending into the patient's glenoid. Because the rasp may be connected to the anvil, the oscillation of the anvil may cause the rasp to oscillate along with the anvil. The oscillation of the rasp may smooth the neoglenoid in preparation for a glenoid implant.

In another aspect, a method of preparing a glenoid of a patient for receiving a biconvex glenoid implant may include fastening a base of a reaming device to a paleoglenoid portion of the glenoid, and translating a rasp of the reaming device in a proximal-distal direction relative to the base while the base is fastened to the paleoglenoid portion of the glenoid. The method may further include driving the rasp to ream a neoglenoid portion of the glenoid.

In some arrangements, translating the rasp may include translating the rasp between a first pre-set position and a second pre-set position.

In some arrangements, the first pre-set position may correspond to a first size biconvex glenoid implant, and the second pre-set position corresponds to a second size biconvex glenoid implant, the second size being different than the first size.

In some arrangements, driving the rasp may include driving the rasp to move repeatedly relative to a pivot axis.

In some arrangements, the reaming device may include an assembly for transferring rotational input on a shaft into oscillating motion of the rasp about a pivot axis.

In some arrangements, the assembly may include a hammer offset from a central axis of the shaft and an anvil connected to the rasp, the anvil including a pair of prongs extending adjacent to the hammer.

In another aspect, a reaming device for preparing a glenoid of a patient may include a base configured for mounting to bone and an oscillatory rasp configured to be translatable in a proximal-distal direction relative to the base while the base is coupled to the glenoid of the patient.

In some arrangements, the device may include a shaft drivable to rotate about its centerline and including a hammer offset from the centerline, and an anvil to which the rasp is mounted. The anvil may be rotatable about a pivot axis and including two prongs extending along the hammer.

In some arrangements, the prongs may extend along opposite sides of the hammer.

In some arrangements, the centerline of the shaft may extend parallel to the proximal-distal direction.

In some arrangements, the anvil may be adjustable along the proximal-distal direction relative to the base.

In some arrangements, the rasp may be adjustable along the proximal-distal direction between a plurality of discrete lockable positions.

In some arrangements, the discrete lockable positions may be defined by a peg and hole interface including a plurality of holes in the device. The holes may be mutually spaced apart relative to one another along the proximal-distal direction.

In some arrangements, the rasp may be pivotably connected to the peg of the peg and hole interface.

In some arrangements, the discrete lockable positions may correspond to appropriate reaming depths of a preselected plurality of glenoid implants having biconvex surfaces mimicking differing degrees of eccentric glenoid erosion.

In some arrangements, the rasp may extend at an angle relative to a surface of the base configured to mate to a paleoglenoid corresponding to an angle at which a portion of a glenoid implant configured to mate to a prepared neoglenoid extends relative to a portion of the glenoid implant configured to mate to a prepared paleoglenoid.

In some arrangements, the angle at which the rasp extends relative to the surface of the base configured to mate to the paleoglenoid may be between 20° and 40°.

In some arrangements, the angle at which the rasp extends relative to the surface of the base configured to mate to the paleoglenoid may be 30°.

In another aspect, a reaming device for preparing a glenoid of a patient may include a shaft drivable to rotate about its centerline and including a hammer offset from the centerline. The device may further include an anvil including two prongs extending along the hammer. The anvil may be rotatable about a pivot axis. A rasp may be connected to the anvil so that rotating the shaft causes oscillation of the rasp, the rasp including a raised portion and a recessed portion both including teeth. The teeth included in the raised portion may have a greater height relative to a base of the rasp than the teeth included in the recessed portion. The rasp may be configured to be translated in a proximal-distal direction parallel to the centerline of the shaft while the reaming device is coupled to the glenoid of the patient.

In another aspect, a bone reaming device may include a base fastenable to bone and extending generally parallel to a proximal-distal axis and a rasp rotatably drivable about a rasp axis. The rasp axis may be translatable relative to the base and the rasp receives driving input from a drive shaft through at least one ball joint.

BRIEF DESCRIPTION OF THE DRAWINGS

FIG. 4A is a cross-sectional view of an exemplary peg and hole assembly that may be included in the device of FIGS. 2A-3.

FIG. 4B is a cross-sectional view of an exemplary pin and hole assembly that may be included in the device of FIGS. 2A-3.

DETAILED DESCRIPTION

When referring to specific directions and planes in the following disclosure, it should be understood that, as used herein, the term "proximal" means closer to the operator/surgeon, and the term "distal" means further away from the operator/surgeon. The term "anterior" means toward the front of the body or the face, and the term "posterior" means toward the back of the body. With respect to the longitudinal axis of the spine, the term "superior" refers to the direction towards the head, and the term "inferior" refers to the direction towards the pelvis and feet. The "transverse plane" is that plane which is orthogonal to the longitudinal axis of the spine. The "coronal plane" is a plane that runs from side to side of the body along the longitudinal axis of the spine and divides the body into anterior and posterior portions. The "sagittal plane" is a plan that runs along the longitudinal axis of the spine and defines a plane of symmetry that separates the left and right sides of the body from each other. Finally, "medial" refers to a position or orientation toward the sagittal plane, and lateral refers at a position or orientation relatively further from the sagittal plane.

Figure 2A:
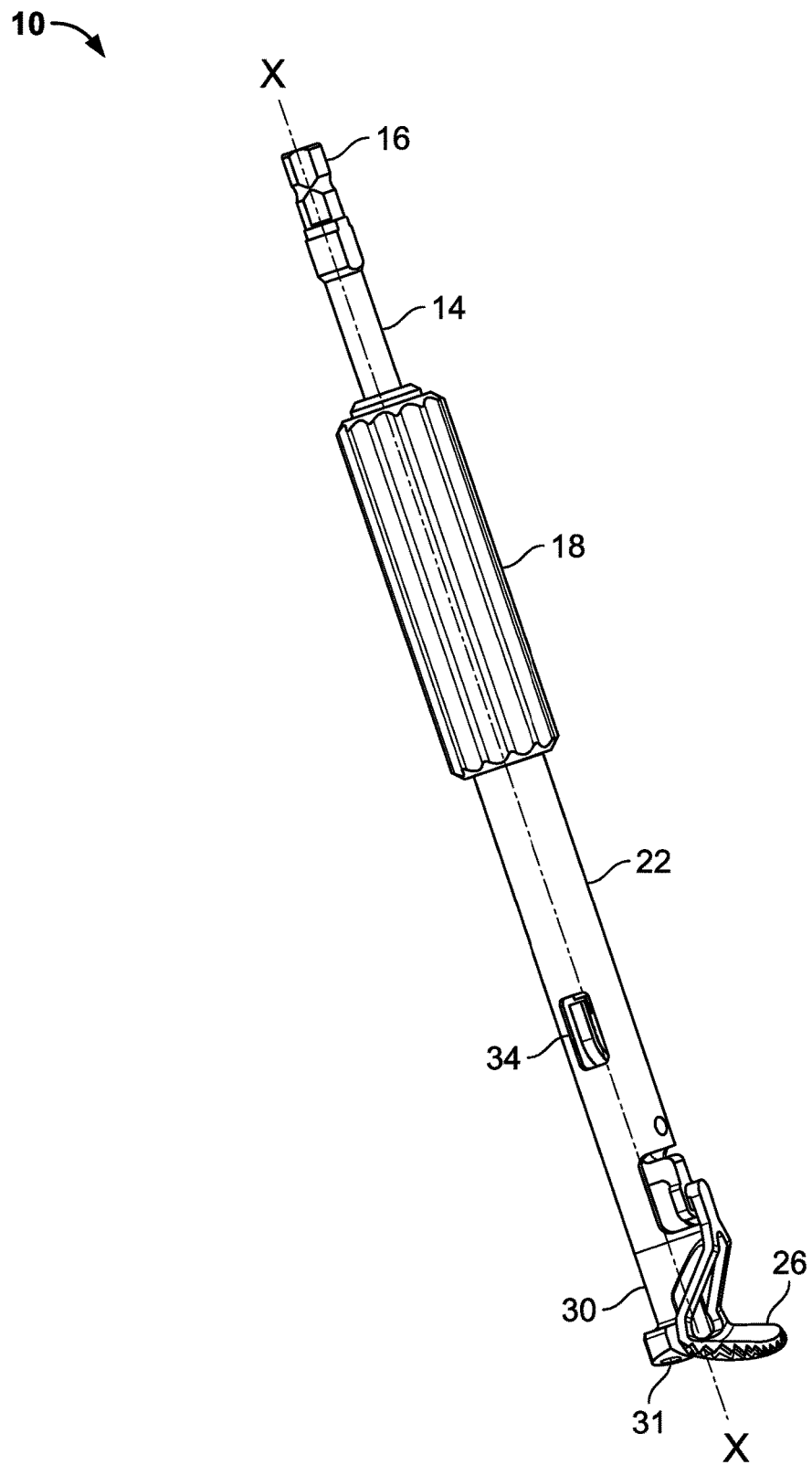
FIG. 2A is an oblique side view of a device according to a first aspect of the disclosure.
Figure 2B:
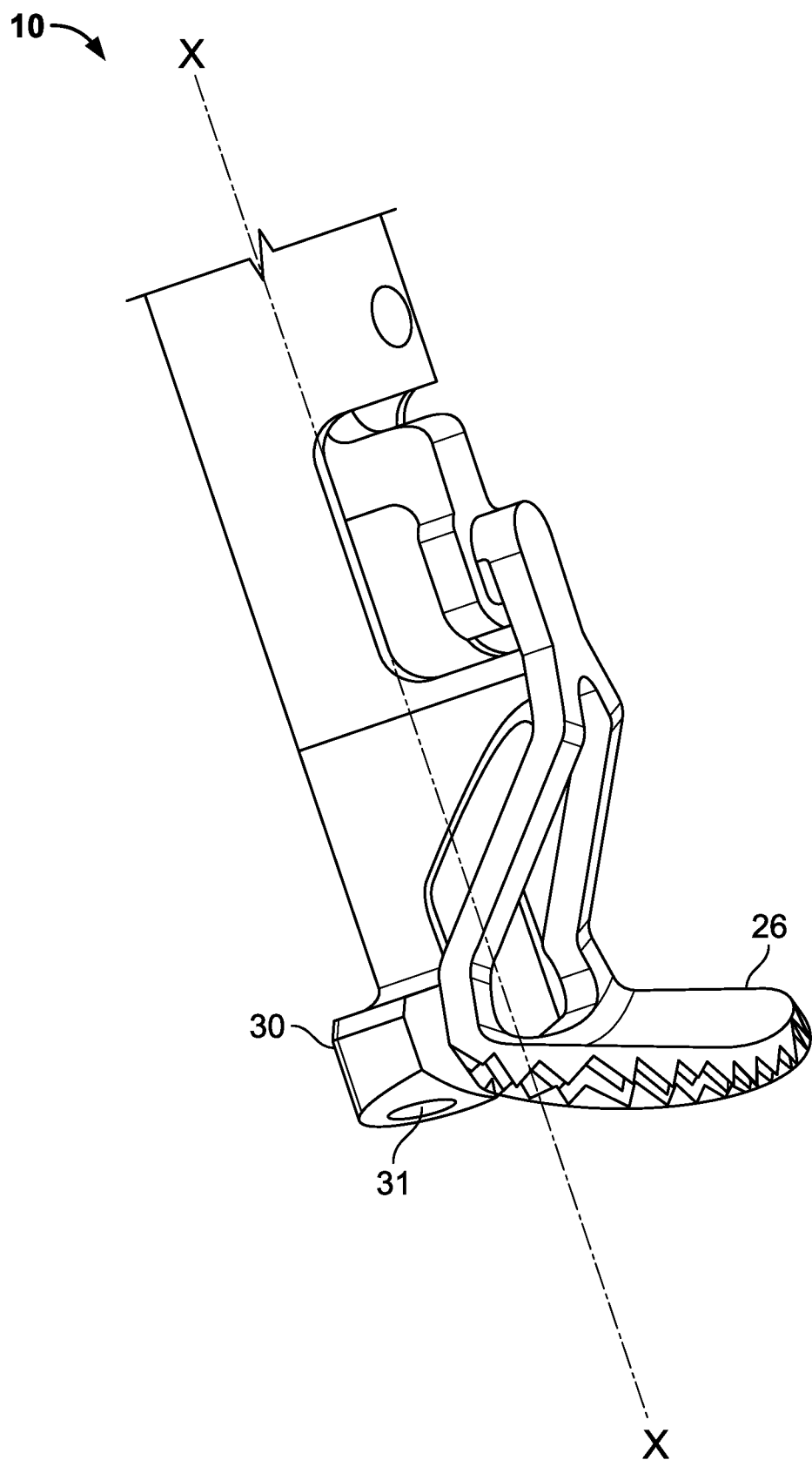
FIG. 2B is a close view of a rasp of the device of FIG. 2A.

A bone preparation device 10 is shown in FIG. 2. The device 10 includes a shaft 14 extending along an axis of rotation X, which is also the shaft's centerline in the illustrated example. In the illustrated arrangement, the axis of rotation X is aligned with a proximal-distal axis of the device 10. However, in other arrangements, the axis of rotation may be transverse to or offset from the proximal-distal axis of the device 10. A drive head 16 provides a proximal end of the shaft 14. The drive head 16 shown in FIG. 2 has a hexagonal axial cross-section, but other shapes of drive head 16 are contemplated.

The shaft 14 extends through a grip 18 and a tube 22 extending distally beyond the grip 18. A rasp 26 and base 30 extend distally beyond a distal end of the tube 22. The rasp 26 may be configured to ream or otherwise prepare bone on the neoglenoid portion of a native glenoid with eccentric glenoid erosion. In the illustrated example, and as may be better appreciated by the close view provided by FIG. 2B, the rasp 26 extends at an angle relative to the base 30 that corresponds to the angle at which the second convex surface 3b of a selected implant extends relative to the first convex surface 3a. The base 30 shown in FIGS. 2A and 2B includes a hole 31, such as for encircling a bone screw for fixing the base to the paleoglenoid portion of a native glenoid with eccentric glenoid erosion. The tube 22 may include two windows 34 on opposite sides of the tube 22 (only one window 34 being visible in the view presented in FIG. 2).

Figure 3:
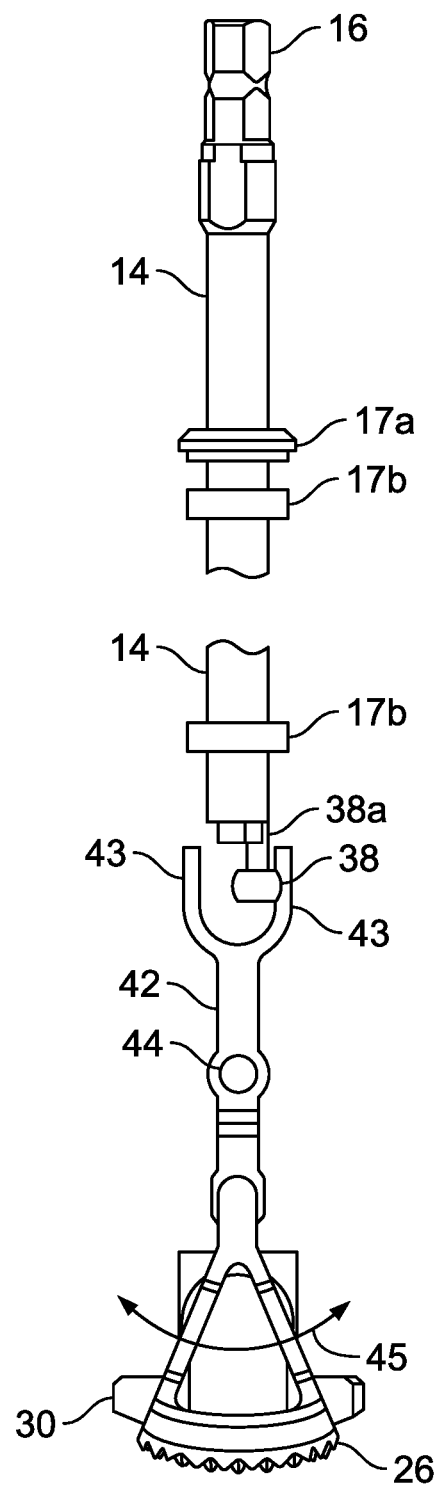
FIG. 3 is a front elevation view of certain components of the device of FIGS. 2A and 2B.

The grip 18 and tube 22 are not shown in FIG. 3. As shown in FIG. 3, the shaft 14 includes a cap 17*a* for sitting atop the grip 18, thereby restraining movement along the proximal-distal axis X of the shaft 14 relative to the grip 18. Two bearings 17*b* encircle the shaft 14 to maintain alignment of the shaft 14 within the grip 18 and the tube 22 while allowing the shaft 14 to rotate. A hammer 38 extends from a distal end of the shaft 14. The hammer 38 extends along an axis that is offset from the axis of rotation X of shaft 14.

An anvil 42 is disposed distally of the shaft 14 and supported on a generally cylindrical pivot pin 44. The pivot pin 44 may extend through a generally cylindrical channel within the anvil 42, tube 22, and/or a connecting apparatus connected to the anvil 42 or tube 22, such that the anvil 42 is pivotable relative to the tube 22. The anvil 42 includes two prongs 43 extending proximally on opposite sides of the hammer 38 in a horseshoe or general "U"-shape. When the shaft 14 rotates about axis X, the hammer 38 also rotates about axis X. However, due to the offset between the axis of hammer 38 and axis X, the hammer 38 follows a relatively large arcuate pathway during rotation, alternately striking the two prongs 43 as the hammer 38 traverses the path of rotation. In some alternative arrangements, the anvil 42 may have only one prong 43, resulting in a relatively low oscillation speed.

In the illustrated arrangement, when the shaft 14 rotates, the hammer 38 moves along a path of travel. The anvil 42 is constrained relative to the shaft 14 such that neither prong 43 can travel closer to the axis of rotation X than the hammer's 38 path of travel. Instead, the prongs 43 may only move so far toward the axis of rotation X such that an inner edge of a prong 43, relative to the axis of rotation X, may be contacted by an outer edge of the hammer 38 while the shaft 14 rotates. When the hammer 38 strikes the inner edge of a prong 38, the prong 38 is driven away from the axis of rotation X, causing the anvil 44 to pivot about the pivot axis. The pivoting of the anvil 44 brings the opposite prong 43 into the hammer's 38 striking range. Thus, the hammer 38 strikes the prongs 43 in alternation.

In some arrangements, a stem 38*a* that connects the hammer 38 to the shaft 14 enables the hammer 38 to rotate relative to the stem 38*a*. The rotatable connection between the hammer 38 and the stem 38*a* enables the hammer 38 to roll across the prongs 43 as it strikes them.

The alternating striking of the prongs 43 causes the anvil 44 to pivot back and forth about a pivot axis defined along the pivot pin 44 in an oscillating pattern 45. The pivoting of the anvil 42 transfers to oscillation of the rasp 26, which is connected to the anvil 42. The arrangement of the hammer 38 and anvil 44 thereby converts rotational input on the drive head 16 of the shaft 14 to oscillation of the rasp 26. In the illustrated arrangement, the oscillating pattern 45 includes the prongs 43 alternatingly passing through a respective one of the windows 34.

The rasp 26 and base 30 are moveable proximally and distally relative to one another. In some arrangements, the base 30 is moveably coupled to the tube 22. In some such arrangements, the base 30 has an interference fit within a part of the tube 22 such that the base 30 may slide relative to the tube 22 while generally being held frictionally in place. In further such arrangements, such as shown in FIGS. 4A and 4B, the tube 22 has a series of detents or holes 22*a* for selectively engaging the base 30 at various positions. In the arrangement shown in FIG. 4A, the base 30 includes a peg 30*a* that may engage any of the holes 22*a* to fix the base 30 at one of multiple discrete positions relative to the tube 22. The portion of the tube 22 containing the holes 22*a* or portion of the base 30 to which the peg 30*a* is attached may be elastically deformable so that the peg 30*a* may be selectively engageable with any of the holes 22*a*. In the arrangement shown in FIG. 4B, the base 30 includes an opening 30*b* and a fastener 32 extends through the opening 30*b* and one of the holes 22*a* to fix the base 30 at one of multiple discrete positions relative to the tube 22. In various other arrangements, the base 30 includes a series of detents or holes similar to the holes 22*a* shown in FIGS. 4A and 4B, and either the tube 22 includes a peg or the device 10 is provided with a fastener for engaging the tube 22 to the base 30.

In other arrangements, axial motion of the rasp 26 relative to the base 30 may be accomplished by movement of the anvil 42 relative to the tube 22. In various embodiments, the tube 22 includes multiple possible points of fixation for the pivot pin 44, or the pivot pin 44 is connected to the tube 22 by other suitable adjustable features.

Figure 5:
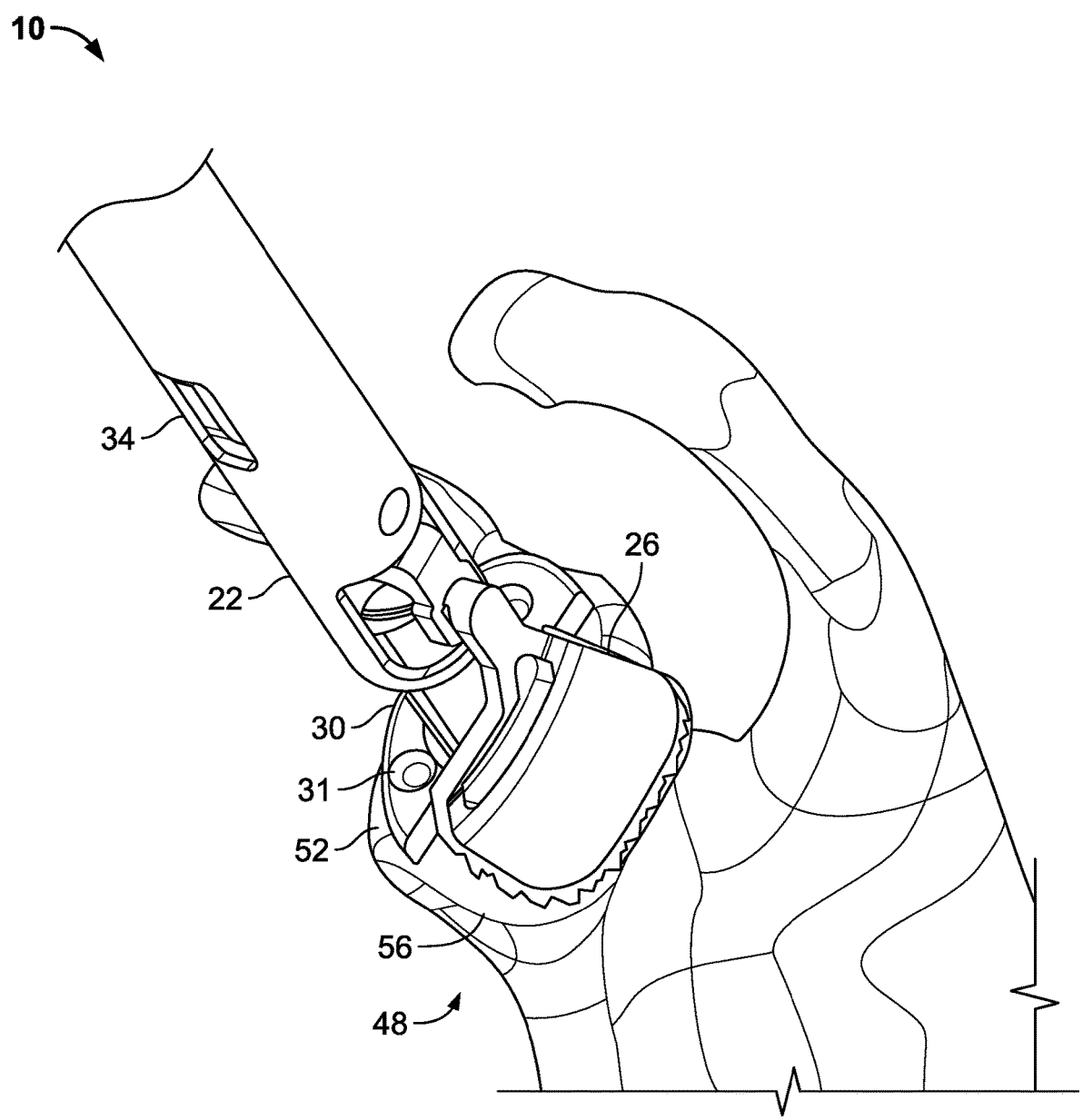
FIG. 5 is an oblique perspective view of the device of FIGS. 2A-3 in an exemplary use case.

Turning to FIG. 5, the device 10 is shown positioned on a native glenoid 48 such that the base 30 is fastened to a paleoglenoid 52, while the rasp 26 is disposed against a neoglenoid 56. The rasp 26 extends distally beyond the base 30 to reach the neoglenoid 56, enabling the raps 26 to prepare the neoglenoid 56 largely without affecting the paleoglenoid 52.

Figure 1A:
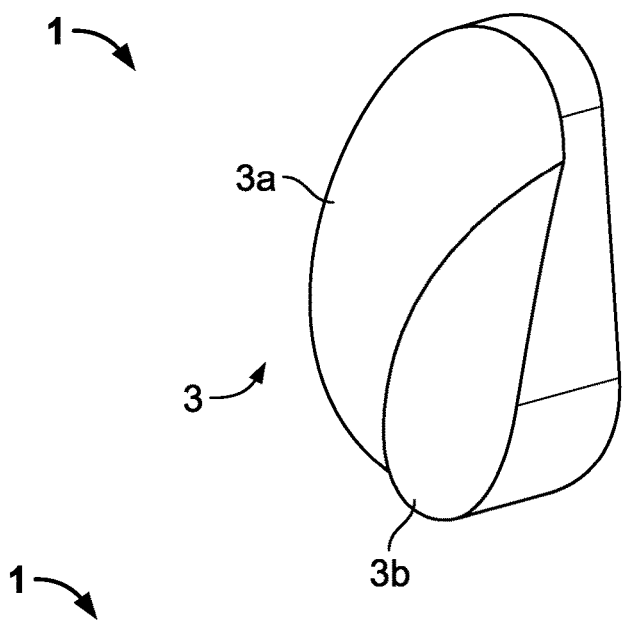
FIG. 1A is an oblique top view of an exemplary glenoid implant having a biconvex bone-contacting surface.
Figure 1B:
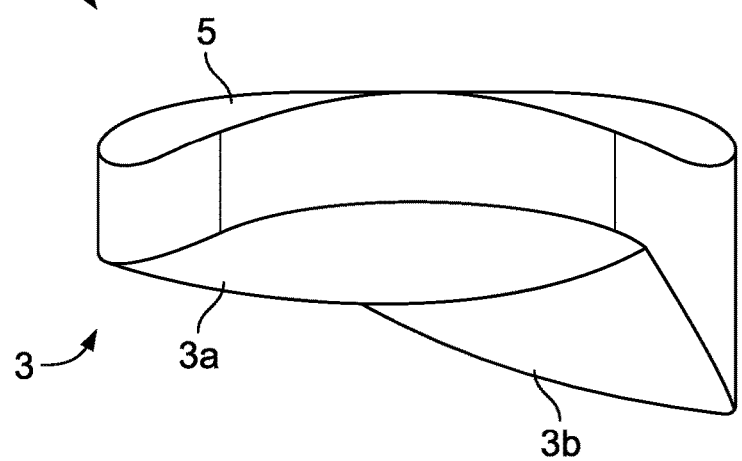
FIG. 1B is a side elevation view of the glenoid implant of FIG. 1A.
Figure 1C:
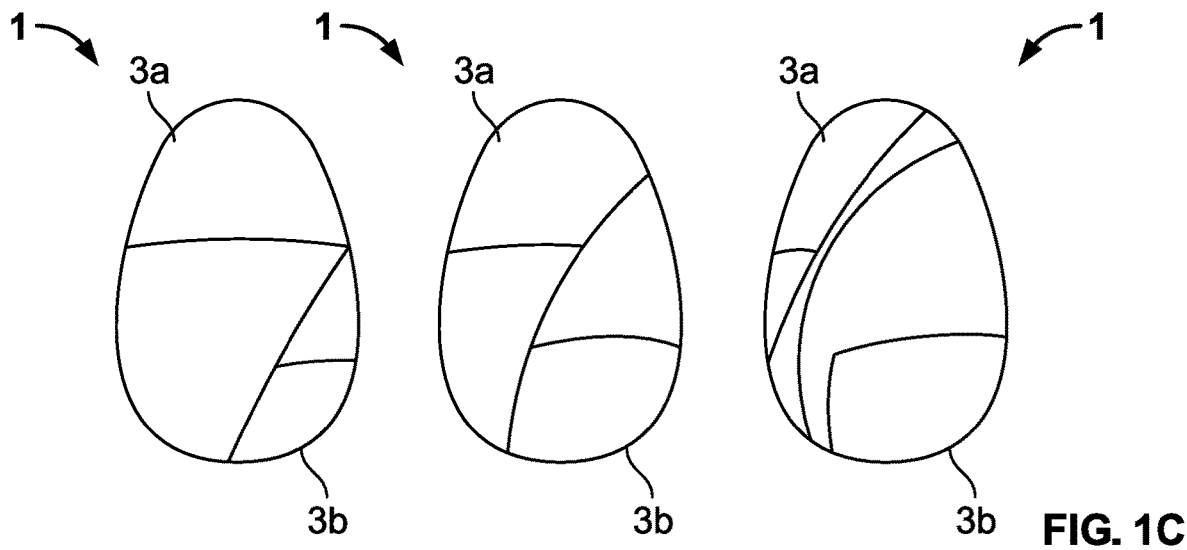
FIG. 1C is a bottom view of three exemplary glenoid implants having biconvex bone-contacting surfaces.

A method of using the device 10 includes fastening the base to the paleoglenoid 52. The base 30 may be fastened to the paleoglenoid 52 before or after the paleoglenoid 52 is smoothed, reamed, and/or otherwise prepared for a glenoid implant, such as an augmented biconvex glenoid implant similar to the implant illustrated in FIGS. 1A-B. The paleoglenoid may be smoothed or prepared with any known suitable reaming method. The rasp 26 is adjusted relative to the base 30 before, after, or both before and after the base 30 is fastened to the paleoglenoid 52 such that the rasp 26 is disposed against the neoglenoid 56. It should be understood that augmented glenoid implants may be provided in different sizes that may generally correspond to different levels of eccentric glenoid erosion. For example, a native glenoid with a relatively small amount of eccentric glenoid erosion may be treated with an augmented glenoid implant with a relatively small neoglenoid portion, while a native glenoid with a relatively large amount of eccentric glenoid erosion may be treated with an augmented glenoid implant with a relatively large neoglenoid portion. The plunge depth of the rasp 26 relative to the base 30 (i.e. the distance which the rasp 26 extends distally beyond the base 30) may be set to generally correspond to the size of the augmented glenoid implant and the level of eccentric glenoid erosion. For example, if the augmented glenoid is provided in three sizes that correspond to three levels of eccentric glenoid erosion, the rasp 26 may have three pre-set plunge depths relative the base 30, each plunge depth corresponding to an available size of the augmented glenoid implant. Still further, it should be understood that the different levels of reaming of the neoglenoid (resulting from the particular plunge depth of the rasp 26) may generally follow the progression of eccentric glenoid erosion. In other words, as eccentric glenoid erosion progresses and/or worsens, the depth of the neoglenoid increases, while the transition line between the paleoglenoid and the neoglenoid also shifts. The different plunge depths of the rasp 26 result in reaming that generally follows the anatomic progression of eccentric glenoid erosion, allowing a relatively small amount of bone stock to be removed during preparation of the glenoid to receive an augmented glenoid implant.

With the rasp 26 positioned at the desired plunge depth relative to the base 30, the shaft 14 is driven to rotate about the axis of rotation X, thereby causing the rasp 26 to oscillate. The oscillation of the rasp 26 grinds or cuts away portions of the neoglenoid 56 to leave a smoother surface and to prepare the neoglenoid 56 for reception of the augmented glenoid implant. If necessary, the rasp 26 may be adjusted after some initial reaming of the neoglenoid 56 to re-engage the rasp 26 with the neoglenoid 56 to facilitate further grinding or cutting of the neoglenoid 56. This change in plunge depth may be performed without needing to disengage the base 30 from the paleoglenoid 52. Positioning and grinding steps may be alternated as necessary until the neoglenoid 56 is prepared for implantation of the glenoid implant.

The particular geometry of the rasp 26 illustrated in FIGS. 2A-5 is merely exemplary. The rasp 26 may be replaced between each procedure, and rasps 26 used with the device may have varying sizes and angles as appropriate for the patient. For example, a rasp 26 may be selected based on the respective geometry of the patient's paleoglenoid 52 and neoglenoid 56, or the rasp 26 may be selected based on the biconvex profile of a chosen glenoid implant. In various exemplary arrangements, the rasp 26 extends at a 30° angle relative to the axis of rotation X, or at an angle between about 20° and about 40° relative to the axis of rotation X, or at an angle that is adjustable, for example by adjustment of a connection between the rasp 26 and the anvil 42. However, in the illustrated embodiment, the angle is fixed and the axial adjustment of the rasp 26 is sufficient to provide the desired level of glenoid preparation based on the level of eccentric glenoid erosion in the patient.

Figure 6:
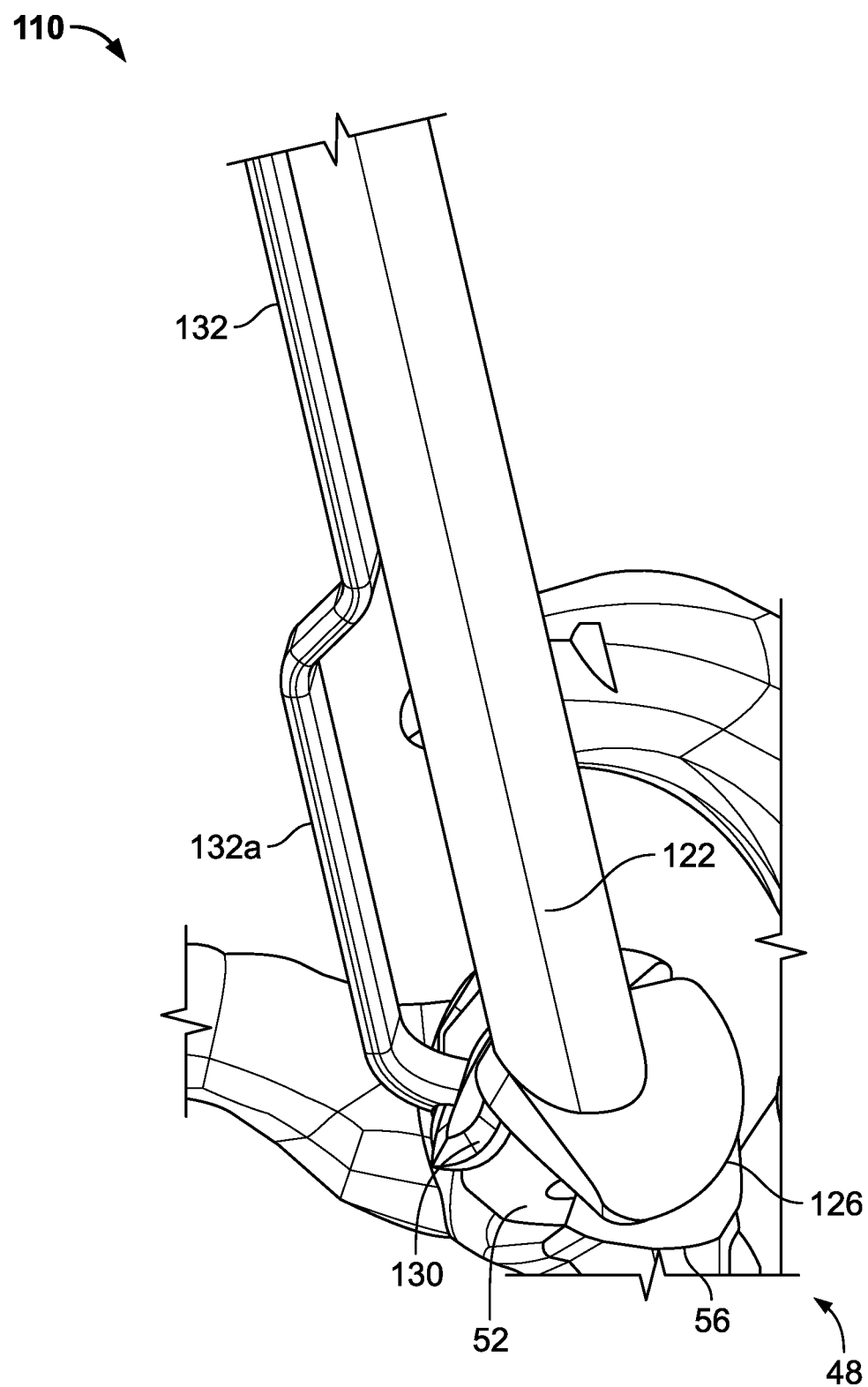
FIG. 6 is an oblique perspective view of a device according to a second aspect of the disclosure in an exemplary use case.

A bone preparation device 110 according to a second arrangement as shown in FIG. 6 similarly includes a tube 122, rasp 126, and base 130. The base 130 further includes an arm 132 extending proximally from the base 130 to connect to the tube 122 through features not shown. The arm 132 includes an offset portion 132a that provides clearance so that the rasp 126 can oscillate. Like the base 30 of the device 10 of FIGS. 2-5, the base 130 of the device 110 illustrated in FIG. 6 is moveable proximally or distally relative to the rasp 126. However, the base 130 is connected to the tube 122 and rasp 126 by features located proximally from the rasp 126 and distal end of the tube 122.

Figure 7:
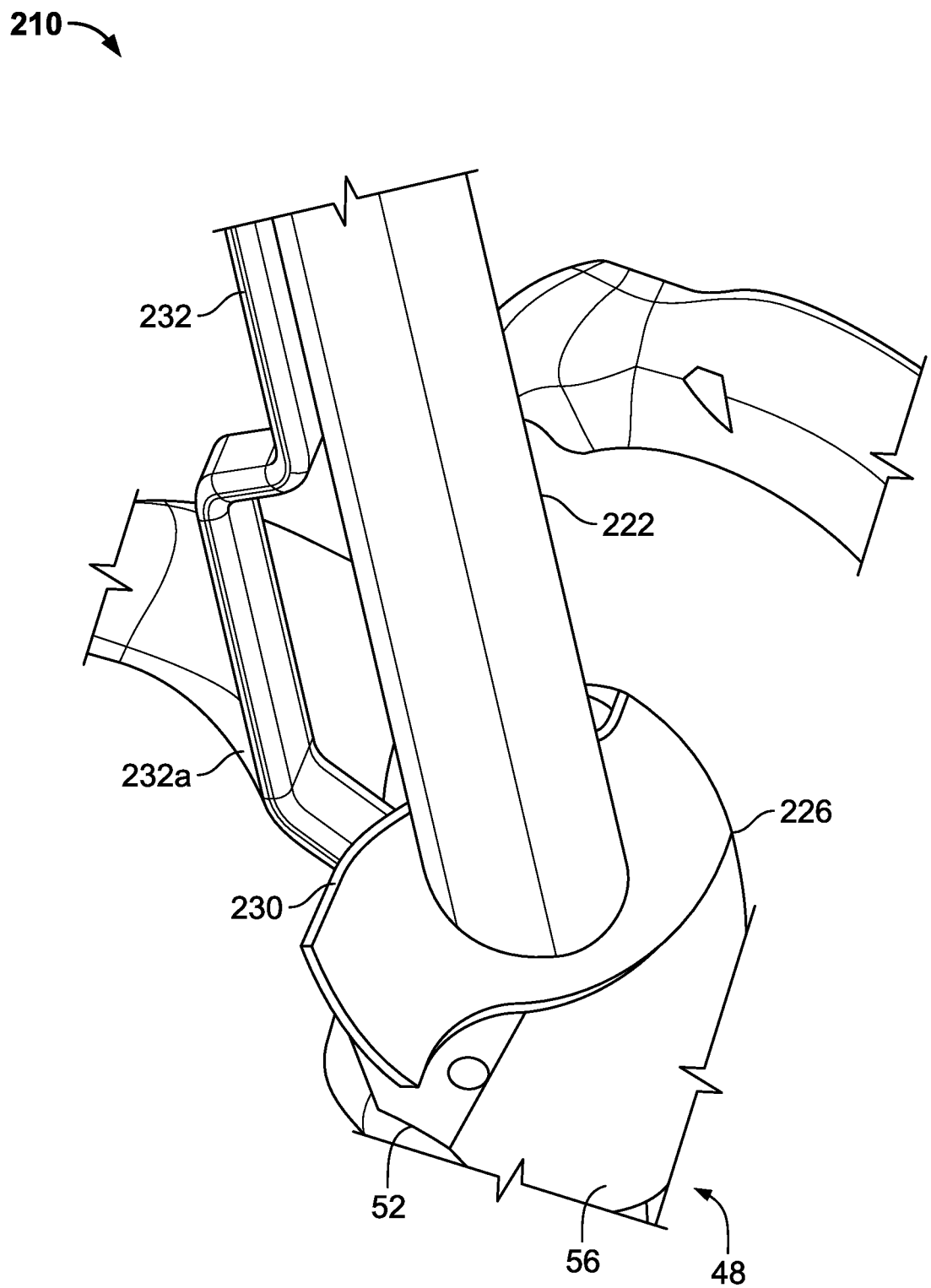
FIG. 7 is an oblique perspective view of a device according to a third aspect of the disclosure in an exemplary use case.

A bone preparation device 210 according to a third arrangement as shown in FIG. 7 includes a tube 222, base 230, and arm 232 with an offset portion 232a similar to those of the device 110 shown in FIG. 6. In contrast to the devices 10, 110 shown in FIGS. 2-5, the device 210 of the arrangement shown in FIG. 7 includes a rotary rasp 226. The device 210 lacks the hammer 38 and anvil 42 of device 10. Instead, rotational input to the device 210, such as on features similar to the shaft 14 and drive head 16, is used to drive the rasp 226 to rotate. The offset portion 232b accommodates the rotation of the rasp 226.

Figure 8:
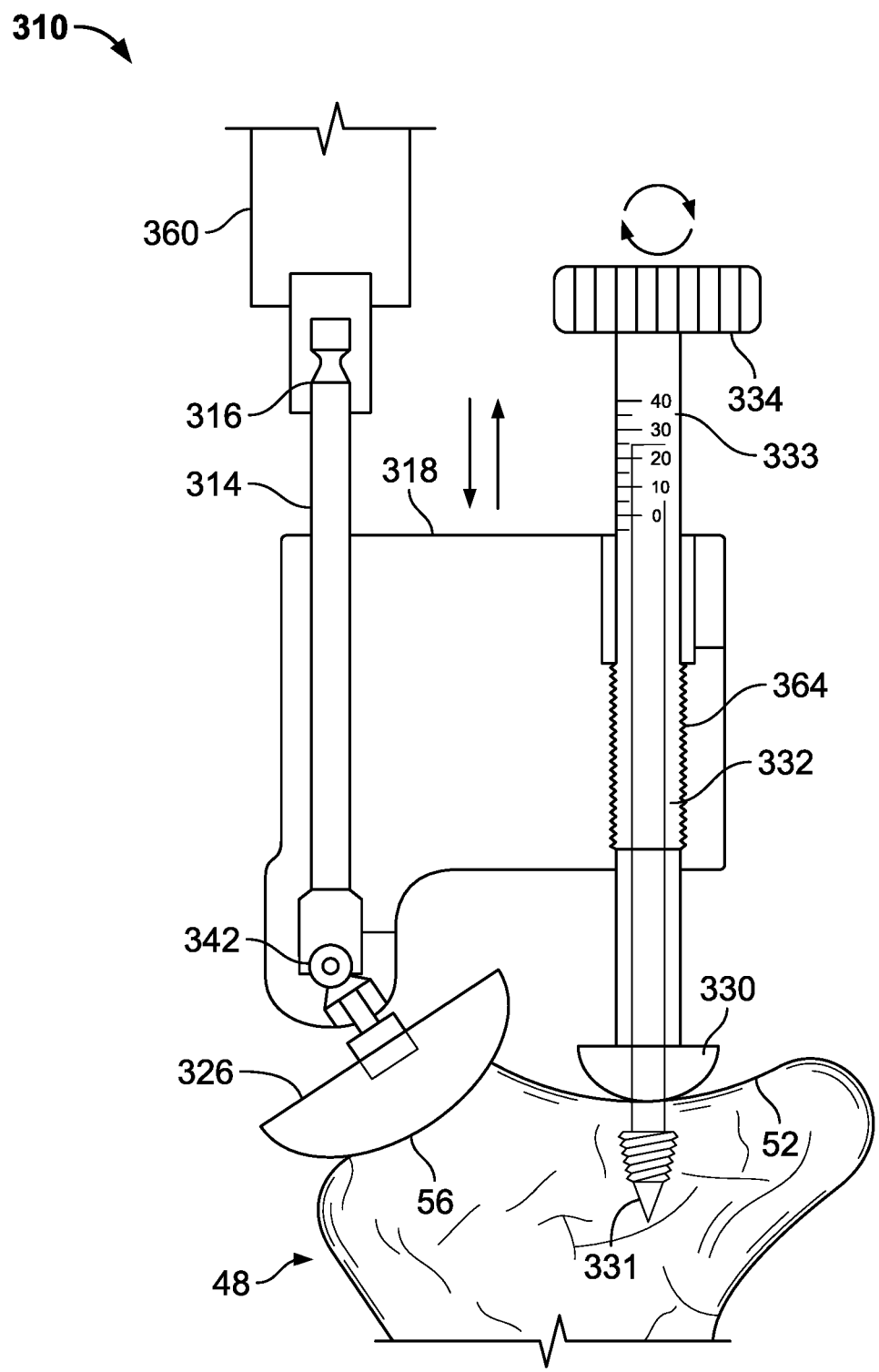
FIG. 8 is a cross-sectional view of a device according to a fourth aspect of the disclosure in an exemplary use case.

A bone preparation device 310 according to another embodiment is shown in FIG. 8. The device 310 includes a carriage 318 that holds parallel, or generally parallel, a drive shaft 314 and a base shaft 332. The base shaft 332 includes an anchor 331, which includes a spike and screw thread in the illustrated arrangement, at its distal end. The base shaft 332 further includes a cap 330 that limits the distance the base shaft can be driven into a paleoglenoid 352. After insertion into the paleoglenoid 352, the base shaft 332 is inserted into a threaded sleeve 333 that is engaged with a threaded bore 364 within the carriage 318. A knob 334, located at a proximal end of the threaded sleeve 333 in the illustrated arrangement, facilitates rotation of the threaded sleeve 333 relative to the carriage 318. Rotation of the threaded sleeve 333 within the threaded bore 364 pushes down against the base shaft 332 and causes the carriage 318, the drive shaft 314, and a reamer 326 to translate relative to the base shaft 332 and paleoglenoid 352. A ball joint 342 joins the reamer 326 to the drive shaft 314. The ball joint 342 is configured to allow the reamer 326 to be rotatable with two degrees of freedom relative to the ball joint 342, but transmits rotation from the drive shaft 314 to the reamer 326 such that rotational input from a motor or power tool 360 engaged with a drive head 316 at a proximal end of the drive shaft 314 causes the reamer 326 to rotate.

Figure 9:
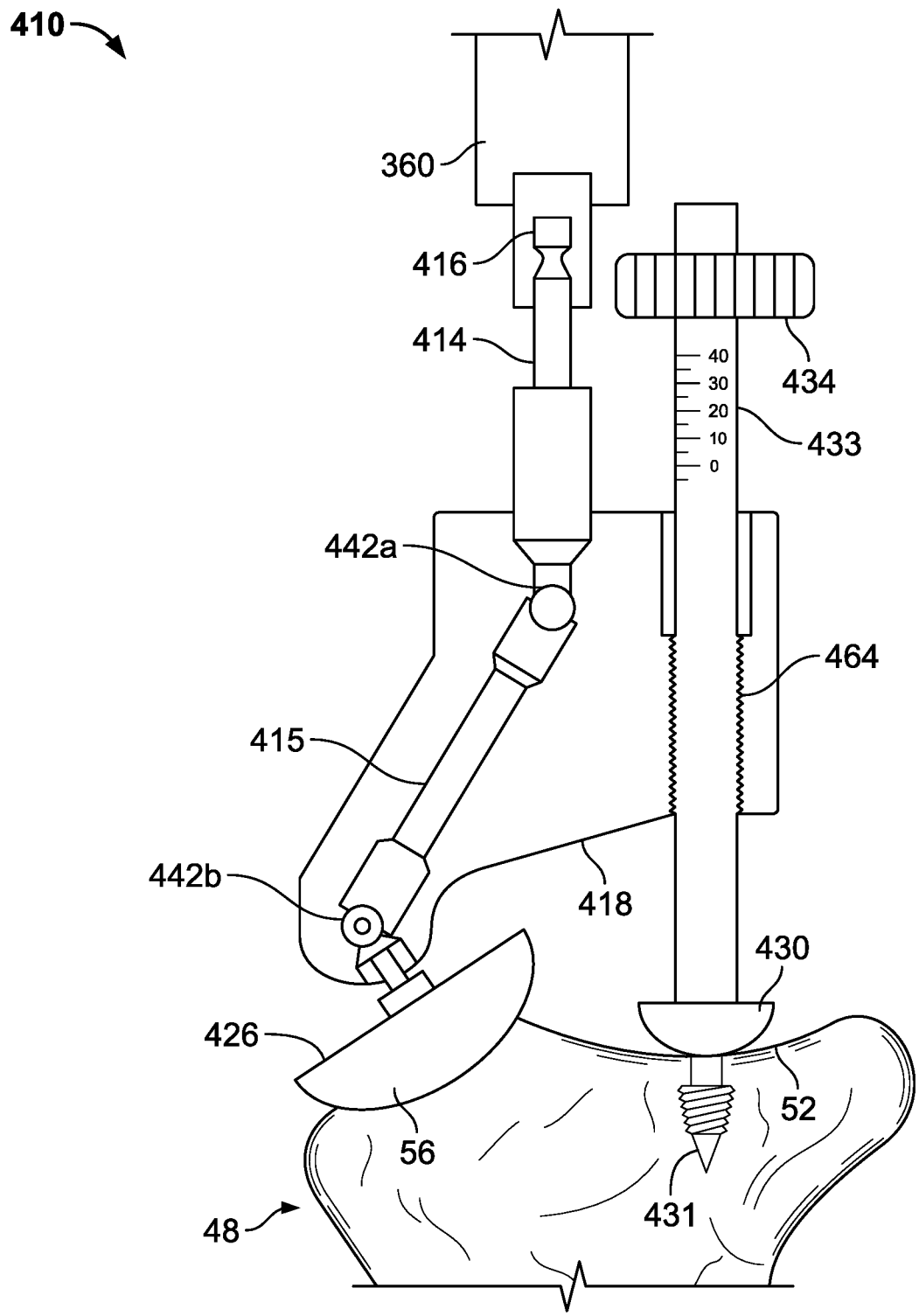
FIG. 9 is a cross-sectional view of a device according to a fifth aspect of the disclosure in an exemplary use case.

A bone preparation device 410 according to another embodiment is shown in FIG. 9. The device 410 includes reamer 426 that is rotationally drivable through a proximal ball joint 442a and distal ball joint 442b. The proximal ball joint 442a connects a drive shaft 414 to an intermediate shaft 415, and the distal ball joint 442b connects the intermediate shaft 442b to the reamer 426. Together, the first ball joint 442a and second ball joint 442b operate to provide the reamer 426 with six degrees of freedom relative to an anchor 431 for securing the device 410 to the paleoglenoid 52. The device 410 further includes a drive head 416, carriage 418, cap 430, base shaft (not illustrated), sleeve 433, knob 434, and threaded bore 464, which are generally similar to the drive head 316, carriage 318, cap 330, base shaft 332, sleeve 333, knob 334, and threaded bore 364 of FIG. 8, and are thus not described in greater detail herein.

Figure 10A:
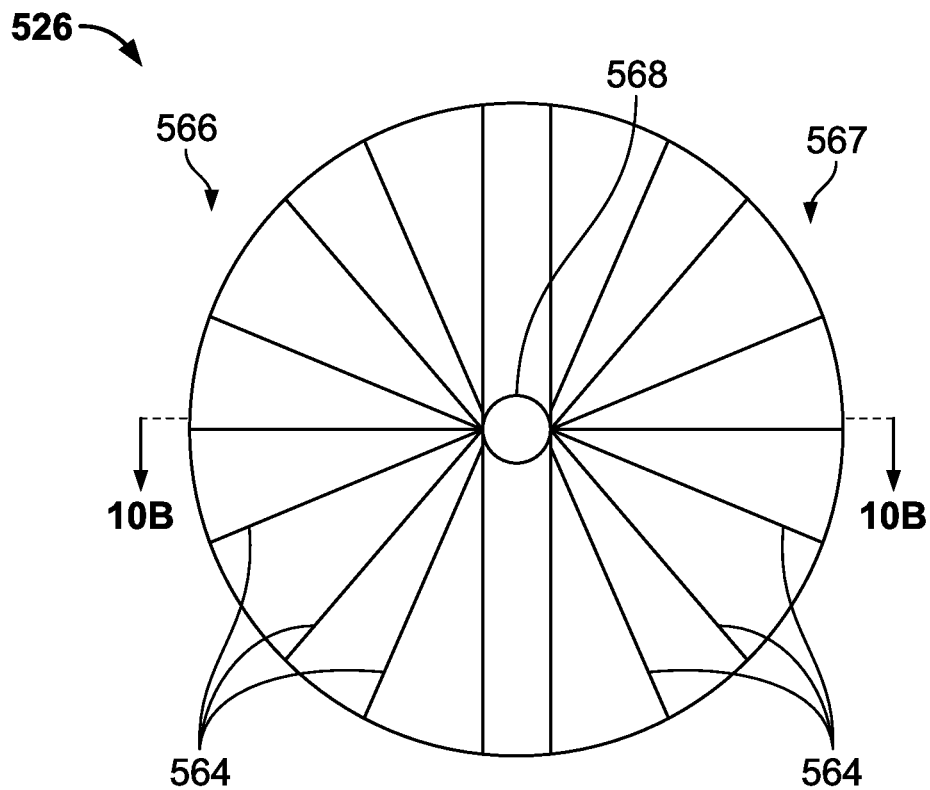
FIG. 10A is a bottom view of a rasp according to a sixth aspect of the disclosure.
Figure 10B:
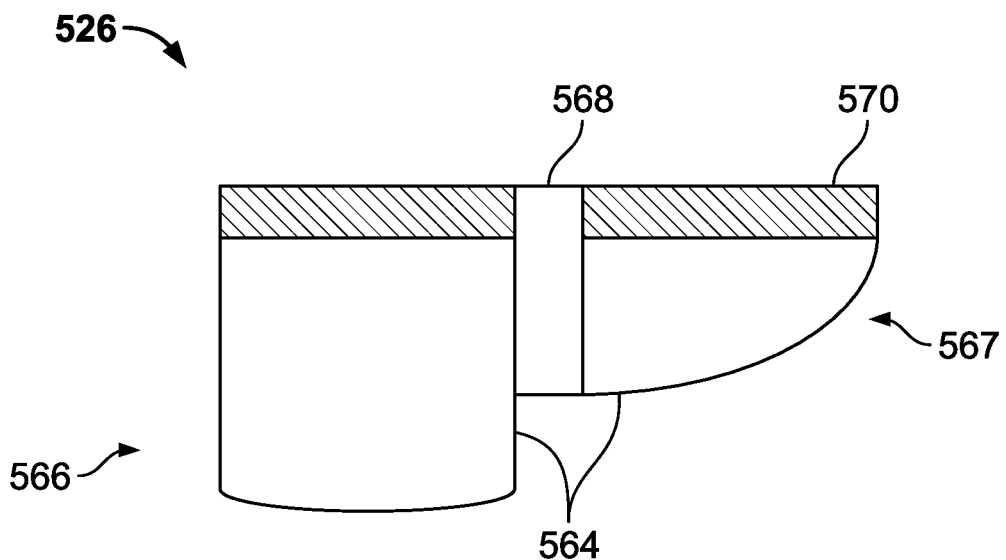
FIG. 10B is a cross-sectional view along line 10B-10B of FIG. 10A.

A rasp 526 according to another arrangement is shown in FIGS. 10A and 10B. As shown in FIG. 10B, the rasp 526 includes a raised portion 566 and a recessed portion 567. Both portions include several teeth 564, but the teeth 564 of the raised portion 566 extend farther from a base 570 of the rasp 526 than the teeth 566 of the recessed portion 567. The differing heights of the raised portion 566 and the recessed portion 567 enable the rasp 526 to prepare the neoglenoid and paleoglenoid simultaneously while oscillating. Specifically, the raised portion 566 can prepare the neoglenoid while the recessed portion 567 prepares the paleoglenoid. Rasps 526 according to the arrangement of FIGS. 10A and 10B may be constructed to correspond to the dimensions of various glenoid implant, such that a height difference between the raised portion 566 and recessed portion 567 of a given rasp 526 corresponds to the biconvex profile of a particular glenoid implant.

The rasp 526 includes a central channel 568 in its base 570 for accommodating a generally cylindrical post or guidewire inserted into the glenoid about which the rasp 566 may oscillate. A similar hammer and anvil assembly may be used for converting rotation to oscillation as that shown in FIG. 3, with the rasp 526 connected to an anvil, except that the anvil would include no pivot pin, thereby permitting the rasp 526 to oscillate about the guidewire or post disposed through the channel 568.

Figure 11:
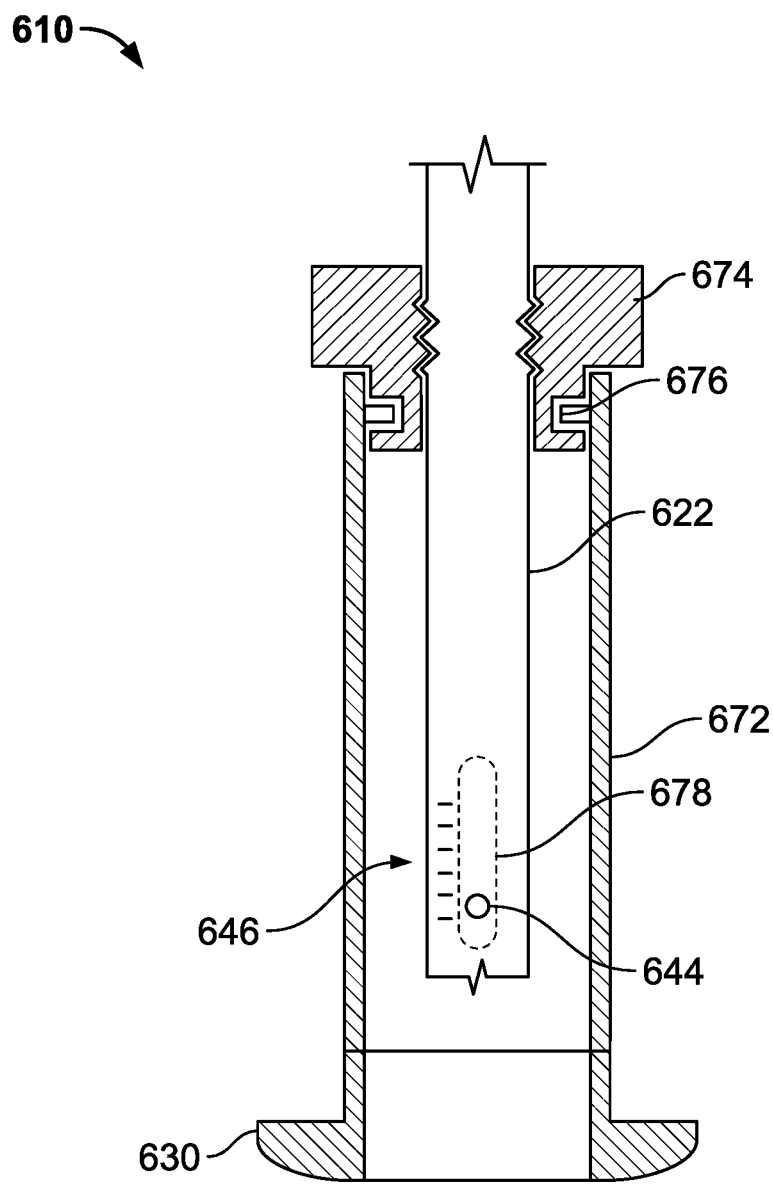
FIG. 11 is a partial cross-sectional side elevation view of a device according to a seventh aspect of the disclosure.

A bone preparation device 610 according to another arrangement is illustrated in FIG. 11. A tube 622 of the bone preparation device 610 is adjustably positionable relative to a housing 672 that ends distally in a base 630. The housing 672 encloses the tube 622, but is shown in cross-section in FIG. 11 to expose the tube 622 for illustrative purposes. The tube 622 is connected to the housing 672 by a nut 674 threadingly engaged to an exterior of the tube 622 and including an annular groove that holds support pins 676 of the housing 672 to suspend the nut rotatably at a fixed axial position relative to the housing 672. An anvil and rasp assembly (not illustrated) similar to that shown in FIG. 3 extends beyond a distal end of the tube 622. A pivot pin 644 of the anvil and rasp assembly, generally similar to the pivot pin 44 for the anvil 42 and rasp 26 of the arrangement shown in FIGS. 2A-5, protrudes from the tube 622 to an axial slot 678 in the housing 672 (shown in dashed lines, as the slot 672 is defined in a portion of the housing 672 rendered transparent for the cross-sectional view of FIG. 11). The extension of the pivot pin 644 through the slot 678 prevents the anvil and rasp assembly, and by extension the tube 622, from rotating about a proximal-distal axis relative to the housing 672 when the nut 674 is turned. Thus, turning the nut 674 causes the threads of the tube 622 to advance within the nut 674, and moves the tube 622 axially relative to the housing 672 and base 630. A position of the anvil and rasp assembly and tube 622 within the housing 672 is observable by the position of a pivot pin 644 within the slot 678. In the illustrated arrangement, indicia 646 are provided on the housing 672 next to the slot 678 to assist determination of the position of the anvil and rasp assembly and tube 622 relative to the housing 672.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of preparing a glenoid of a patient for receiving a biconvex glenoid implant, the method comprising:
    fastening a base of a reaming device to a paleoglenoid portion of the glenoid;
    translating a rasp of the reaming device in a proximal-distal direction relative to the base; and
    driving the rasp to ream a neoglenoid portion of the glenoid.

2. The method of claim 1, wherein translating the rasp includes translating the rasp between a first pre-set position and a second pre-set position.

3. The method of claim 2, wherein the first pre-set position corresponds to a first size biconvex glenoid implant, and the second pre-set position corresponds to a second size biconvex glenoid implant, the second size being different than the first size.

4. The method of claim 1, wherein driving the rasp includes driving the rasp to move repeatedly relative to a pivot axis.

5. The method of claim 1, wherein the reaming device includes an assembly for transferring rotational input on a shaft into oscillating motion of the rasp about a pivot axis.

6. The method of claim 5, wherein the assembly includes a hammer offset from a central axis of the shaft and an anvil connected to the rasp, the anvil including a pair of prongs extending adjacent to the hammer.

7. The method of claim 1, wherein the base extends parallel to a proximal-distal axis, and the rasp is rotatably drivable about a rasp axis, wherein the rasp axis is translatable relative to the base and the rasp receives driving input from a drive shaft through at least one ball joint.

8. A reaming device for preparing a glenoid of a patient, the reaming device comprising:
    a base configured for mounting to bone; and
    an oscillatory rasp configured to be translatable in a proximal-distal direction relative to the base while the base is coupled to the glenoid of the patient, wherein the rasp extends at an angle relative to a surface of the base configured to mate to a paleoglenoid corresponding to an angle at which a portion of a glenoid implant configured to mate to a prepared neoglenoid extends relative to a portion of the glenoid implant configured to mate to a prepared paleoglenoid.

9. The reaming device of claim 8, comprising a shaft drivable to rotate about its centerline and including a hammer offset from the centerline; and
    an anvil to which the rasp is mounted, the anvil being rotatable about a pivot axis and including two prongs extending along the hammer.

10. The reaming device of claim 9, wherein the prongs extend along opposite sides of the hammer.

11. The reaming device of claim 9, wherein the centerline of the shaft extends parallel to the proximal-distal direction.

12. The reaming device of claim 9, wherein the anvil is adjustable along the proximal-distal direction relative to the base.

13. The reaming device of claim 8, wherein the rasp is adjustable along the proximal-distal direction between a plurality of discrete lockable positions.

14. The reaming device of claim 13, wherein the discrete lockable positions are defined by a peg and hole interface including a plurality of holes in the device, the holes being mutually spaced apart relative to one another along the proximal-distal direction.

15. The reaming device of claim 14, wherein the rasp is pivotably connected to the peg of the peg and hole interface.

16. The reaming device of claim 13, wherein the discrete lockable positions correspond to appropriate reaming depths of a preselected plurality of glenoid implants having biconvex surfaces mimicking differing degrees of eccentric glenoid erosion.

17. The device of claim 8, wherein the angle at which the rasp extends relative to the surface of the base configured to mate to the paleoglenoid is between 20° and 40°.

18. The device of claim 17, wherein the angle at which the rasp extends relative to the surface of the base configured to mate to the paleoglenoid is 30°.

19. A reaming device for preparing a glenoid of a patient, the reaming device comprising:
    a shaft drivable to rotate about its centerline and including a hammer offset from the centerline;
    an anvil including two prongs extending along the hammer, the anvil being rotatable about a pivot axis; and
    a rasp connected to the anvil so that rotating the shaft causes oscillation of the rasp, the rasp including a raised portion and a recessed portion both including teeth, wherein the teeth included in the raised portion have a greater height relative to a base of the rasp than the teeth included in the recessed portion,
    wherein the rasp is configured to be translated in a proximal-distal direction parallel to the centerline of the shaft while the reaming device is coupled to the glenoid of the patient.

* * * * *